United States Patent [19]
Clark

[11] Patent Number: 5,990,099
[45] Date of Patent: Nov. 23, 1999

[54] ANGIOSTATIC AGENTS AND METHODS AND COMPOSITIONS FOR CONTROLLING OCULAR HYPERTENSION

[75] Inventor: Abbot F. Clark, Arlington, Tex.

[73] Assignee: Alcon Laboratories, Inc., Forth Worth, Tex.

[21] Appl. No.: 08/994,114

[22] Filed: Dec. 19, 1997

Related U.S. Application Data

[63] Continuation-in-part of application No. 08/990,424, Dec. 15, 1997, abandoned, which is a continuation of application No. 08/643,387, May 6, 1996, Pat. No. 5,698,545, which is a continuation of application No. 08/349,342, Dec. 2, 1994, abandoned, which is a continuation of application No. 07/941,485, Sep. 8, 1992, Pat. No. 5,371,078, which is a continuation-in-part of application No. 07/559,123, Jul. 27, 1990, abandoned, which is a continuation-in-part of application No. 07/419,226, Oct. 10, 1989, abandoned, which is a continuation of application No. 07/264,918, Oct. 31, 1988, Pat. No. 4,876,250.

[51] Int. Cl.$^6$ .......................... A61K 31/58; A61K 31/56
[52] U.S. Cl. ........................ 514/172; 514/173; 514/176; 514/179; 514/180; 514/182
[58] Field of Search .................................. 514/179, 172, 514/173, 176, 180, 182

[56] References Cited

U.S. PATENT DOCUMENTS

| | | | |
|---|---|---|---|
| 4,642,355 | 2/1987 | Nakamura et al. | 548/533 |
| 4,863,912 | 9/1989 | Southren et al. | 514/177 |
| 4,876,250 | 10/1989 | Clark | 514/179 |
| 5,371,078 | 12/1994 | Clark et al. | 514/179 |
| 5,606,043 | 2/1997 | Nguyen et al. | 536/23.5 |
| 5,698,545 | 12/1997 | Clark et al. | 514/179 |

OTHER PUBLICATIONS

Sommer A, et al. Relationship between intraocular pressure and primary open angle glaucoma among white and black Americans. Arch. Ophthalmol. 109:1090–1095, (1991).

Sheffield, et al., "Genetic Linkage of Familial Open Angle Glaucoma to Chromosome 1q21–131," Nature Genetics, 4:47–50 (1993).

Sarfarazi, et al., "Assignment of a Locus (GLC3A) for Primary Congenital Glaucoma (Buphthalmos) to 2p21 and Evidence for Genetic Heterogeneity," Genomics, 30:171–177 (1995).

Akarsu, et al.,"A Second Locus (GLC3B) for Primary Congenital Glaucoma (Buphthalmos) Maps to the 1p36 Region," Human Molecular Genetics, 5(8):1199–1203 (1996).

Stoilova, et al., "Localization of a Locus (GLC1B) for Adult–Onset Primary Open Angle Glaucoma to the 2cen–q13 Region," Genomics, 36:142–150 (1996).

Wirtz, et al., "Mapping a Gene for Adult–Onset Primary Open–Angle Glaucoma to Chromosome 3q," Am. J. Hum. Genet., 60:296–304 (1997).

Andersen, et al., "A Gnee Responsible for the Pigment Dispersion Syndrome Maps to Chromosome 7q35–q36," Arch. Ophthalmol., 115:384–388 (1997).

Richards, et al., "Mapping of a Gene for Autosomal Dominant Juvenile–Onset Open–Angle Glaucome to Chromosome 1q," Am. J. Hum. Genet., 54:62–70 (1994).

Morissette, et al., "A Common Gene for Juvenile and Adult–Onset Primary Open–Angle Glaucomas Confined on Chromosome 1q," Am. J. Hum. Genet., 56:1431–1442 (1995).

Wiggs, et al., "Genetic Linkage of Autosomal Dominant Juvenile Glaucoma to 1q21–q31 in Three Affected Pedigrees," Genomics, 21:299–303 (1994).

Meyer, et al., "Age–Dependent Penetrance and Mapping of the Locus for Juvenile and Early–Onset Open–Angle Glaucoma on Chromosome 1q (GLC1A) in a French Family," Hum. Genet., 98:567–571 (1996).

Graff, et al., "Confirmation of Linkage to 1q21–31 in a Danish Autosomal Dominant Juvenile–Onset Glaucoma Family and Evidence of Genetic Heterogeneity," Hum. Genet., 96:285–289 (1995).

Stone, et al., "Identification of a Gene That Causes Primary Open Angle Glaucoma," Science, 275:668–670 (1997).

Polansky, et al., "Eiconsanoid Production and Glucocorticoid Regulatory Mechanisms in Cultured Human Trabecular Meshwork Cells," The Ocular Effects of Prostaglandins and Other Eicosanoids, pp. 113–138 (1989).

Polansky, et al., "In Vitro Correlates of Glucocorticoid Effects on Intraocular Pressure," Glaucoma Update IV (1991).

Polansky, et al., "Cellular Pharmacology and Molecular Biology of the Trabecular Meshwork Inducible Glucocorticoid Response Gene Product," Ophthalmologica, 211:126–139 (1997).

Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," FEBS Letters, 413:349–353 (1997).

(Kubota, et al., "A Novel Myosin–like Protein (Myocilin) Expressed in the Connecting Cilium of the Photoreceptor: Molecular Cloning, Tissue Expression, and Chromosomal Mapping," Genomics, 41:360–369 (1997).

DeSantis, et al., Dexamethasone–Induction of Ocular Hypertension in the Primate, ARVO Abstracts. Invest. Ophthalmol. Vis. Sci., 31(Suppl.):99 (1990).

Knepper, et al., "Intraocular Pressure and Glycosaminoglycan Distribution in the Rabbit Eye: Effect of Age and Dexamethasone," Exp. Eye Res., 27:567–565 (1978).

Francois, et al., Ultrastructural and Morphometric Study of Corticosteroid Glaucoma in Rabbits, Ophthalmic Res., 16:168–178 (1984).

Lorenzetti, O. J., "Effects of Corticosteroids on Ocular Dynamics in Rabbits," J. Pharmacol. Exp. Therap., 175:763–772 (1970).

(List continued on next page.)

*Primary Examiner*—S. Mark Clardy
*Assistant Examiner*—Alton Pryor
*Attorney, Agent, or Firm*—Sally Yeager

[57] ABSTRACT

Compositions of angiostatic agents for treating GLC1A glaucoma and methods for their use are disclosed.

3 Claims, No Drawings

OTHER PUBLICATIONS

Zhan, et al., "Steroid Glaucoma: Corticosteroid–Induced Ocular Hypertension in Cats," Exp. Eye Res., 54:211–218 (1992).

Rozsival, et al., "Aqueous Humour and Plasma Cortisol Levels in Glaucoma and Cataract Patients," Current Eye Research, 1:391–396 (1981).

Ray, et al., "Plasma Cortisol in Glaucoma," Ann. Ophthalmol., 9:1151–1154 (1977).

Schwartz, et al., "Increased Plasma Free Cortisol in Ocular Hypertension and Open Angle Glaucoma," Arch. Ophthalmol., 105:1060–1065 (1987).

Wilson, et al., Dexamethasone Induced Ultrastructural Changes in Cultured Human Trabecular Meshwork Cells, Cur. Eye Res., 12:784–793 (1993).

Clark, et al., "Glucocorticoid–Induced Formation of Cross–Linked Actin Networks in Cultured Human Trabecular Meshwork Cells," Invest. Ophthalmol. Vis. Sci., 35:281(1994).

Crum, et al., "A New Class of Steroids Inhibits Angiogenesis in the Presence of Heparin or a Heparin Fragment," Science, 230:1375–1378 (Dec. 20, 1985).

Ingber, et al., "A Possible Mechanism for Inhibition of Angiogenesis by Angiostatic Steroids: Induction of Capiullary Basement Membrane Dissolution," Endocrinology, 119:1768–1775 (1986).

Southren, et al., "Intraocular Hypotensive Effect of a Topically Applied Cortisol Metalolite: 3–alpha, 5–beta–tetrahydrocortisol," Investigative Ophthalmology and Visual Science, (May 28, 1987.

Folkman, et al., "Angiostatic Steroids," Ann. Surg., 206(3) (1987).

ANGIOSTATIC AGENTS AND METHODS AND COMPOSITIONS FOR CONTROLLING OCULAR HYPERTENSION

This is a continuation-in-part of application Ser. No. 08/990,424 entitled "Angiostatic Steroids and Methods and Compositions for Controlling Ocular Hypertension" filed on Dec. 15, 1997 and abandoned, which is continuation of Ser. No. 08/643,387 filed May 6, 1996 (issuing Dec. 16, 1997, U.S. Pat. No. 5,698,545), which is a continuation of Ser. No. 08/349,342 filed Dec. 2, 1994 and abandoned, which is a continuation of Ser. No. 07/941,485, filed Sep. 8, 1992 now U.S. Pat. No. 5,371,078 issued Dec. 6, 1994, which is a continuation-in-part of Ser. No. 07/559,123 filed Jul. 27, 1990 and abandoned, which is a continuation-in-part of Ser. No. 07/419,226 filed Oct. 10, 1989 and abandoned, which is a continuation of Ser. No. 07/264,918 filed Oct. 31, 1988 (U.S. Pat. No. 4,876,250).

BACKGROUND OF THE INVENTION

1. Field of the Invention

This invention is directed to the use of angiostatic agents for treating glaucoma or ocular hypertension resulting from altered expression of the GLC1A gene (hereinafter GLC1A or 1q glaucoma) in an individual.

2. Description of Related Art

The glaucomas are a heterogeneous group of optic neuropathies characterized by cupping of the optic nerve head, thinning of the retinal nerve fiber layer due to loss of retinal ganglion cells, and specific pathognomonic changes in visual fields. Elevated intraocular pressure (IOP) is a very important risk factor for the development of most common forms of glaucoma (Sommer A, et al., "Relationship Between Intraocular Pressure and Primary Open Angle Glaucoma Among White and Black Americans," *Arch. Ophthalmol.*, 109:1090–1095, (1991)).

A family history of glaucoma also is an important risk factor for the development of glaucoma. It appears that a significant portion of glaucoma is inherited (or at least the risk for developing glaucoma is inherited) although it is often difficult to establish clear inheritance patterns for most of the glaucomas because of the disease onset late in life and the slowly progressive clinical manifestations of the disease. Despite these problems, a number of families with heritable forms of glaucoma have been identified and these families have been used to map a variety of glaucoma genes (Sheffield, et al., "Genetic Linkage of Familial Open Angle Glaucoma to Chromosome 1q21-q31," *Nature Genetics*, 4:47–50 (1993); Sarfarazi, et al., "Assignment of a Locus (GLC3A) for Primary Congenital Glaucoma (Buphthalmos) to 2p21 and Evidence for Genetic Heterogeneity," *Genomics*, 30:171–177 (1995); Akarsu, et al., "A Second Locus (GLC3B) for Primary Congenital Glaucoma (Buphthalmos) Maps to the 1p36 Region," *Human Molecular Genetics*, 5(8):1199–1203 (1996); Stoilova, et al., "Localization of a Locus (GLC1B) for Adult-Onset Primary Open Angle Glaucoma to the 2cen-q13 Region," *Genomics*, 36:142–150 (1996); Wirtz, et al., "Mapping a Gene for Adult-Onset Primary Open-Angle Glaucoma to Chromosome 3q," *Am. J Hum. Genet.*, 60:296–304 (1997); Andersen, et al., "A Gene Responsible for the Pigment Dispersion Syndrome Maps to Chromosome 7q35-q36," *Arch. Ophthalmol*, 115:384–388 (1997). The first glaucoma gene mapped (GLC1A) was in a large family with autosomal dominant inherited juvenile glaucoma (JG). This disease is characterized by an early disease onset (late teens to early 20s), relatively high IOPs, and general resistance to conventional pharmacological IOP lowering therapy. The GLC1A gene was mapped by positional cloning and linkage analysis to chromosome 1q22-q25 (Sheffield et al, Id), and a number of other groups have confirmed the 1q location of this juvenile glaucoma gene (Richards, et al., "Mapping of a Gene for Autosomal Dominant Juvenile-Onset Open-Angle Glaucoma to Chromosome 1q," *Am. J. Hum. Genet.*, 54:62–70 (1994); Morissette, et al., "A Common Gene for Juvenile and Adult-Onset Primary Open-Angle Glaucomas Confined on Chromosome 1q," *Am. J. Hum. Genet.*, 56:1431–1442 (1995); Wiggs, et al., "Genetic Linkage of Autosomal Dominant Juvenile Glaucoma to lq21-q31 in Three Affected Pedigrees," *Genomics*, 21:299–303 (1994); Meyer, et al., "Age-Dependent Penetrance and Mapping of the Locus for Juvenile and Early-Onset Open-Angle Glaucoma on Chromosome 1q (GLC1A) in a French Family," *Hum. Genet.*, 98:567–571 (1996); Graff, et al., "Confirmation of Linkage to 1q21-31 in a Danish Autosomal Dominant Juvenile-Onset Glaucoma Family and Evidence of Genetic Heterogeneity," *Hum. Genet.*, 96:285–289 (1995). Glaucoma due to the GLC1A gene is often referred to as 1q glaucoma.

The GLC1A gene was identified as encoding a 57 kD protein expressed in the trabecular meshwork (TM) (Stone, et al., "Identification of a Gene That Causes Primary Open Angle Glaucoma," *Science*, 275:668–670 (1997). The expression of the GLC1A gene, and the encoded TM protein, is up-regulated by glucocorticoids (Polansky, et al., "Eicosanoid Production and Glucocorticoid Regulatory Mechanisms in Cultured Human Trabecular Meshwork Cells," *The Ocular Effects of Prostaglandins and Other Elcosanolds*, pp. 113–138 (1989); Polansky, et al., "In Vitro Correlates of Glucocorticoid Effects on Intraocular Pressure," *Glaucoma Update IV* (1991); and Polansky, et al., "Cellular Pharmacology and Molecular Biology of the Trabecular Meshwork Inducible Glucocorticoid Response Gene Product," *Ophthalmologica*, 211:126–139 (1997)). This TM protein is also known as TIGR (trabecular meshwork inducible glucocorticoid response) (Polansky, Id). The glucocorticoid-induction of this TM protein has been suggested to be involved in the generation of glucocorticoid-induced ocular hypertension and glaucoma (Polansky, Id).

The GLC1A gene is expressed in other ocular tissues such as the ciliary epithelium (Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," *FEBS Letters*, 413:349–353 (1997)) and the retina (Kubota, et al., "A Novel Myosin-like Protein (Myocilin) Expressed in the Connecting Cilium of the Photoreceptor: Molecular Cloning, Tissue Expression, and Chromosomal Mapping," *Genomics*, 41:360–369 (1997)). The gene is referred to by several names including GLC1A (Sheffield, supra, Sunden, et al., "Fine Mapping of the Autosomal Dominant Juvenile Open Angle Glaucoma (GLC1A) Region and Evaluation of Candidate Genes," *Genome Research*, 6:862–869 (1996); Stone, et al., supra), TIGR (Polansky supra, Ortego, supra), and myocilin (Kubota, supra). Mutations GLC1A are not only responsible for juvenile glaucoma, but also a significant subset of adult onset primary open angle glaucoma (Stone, et al., supra, Adam, et al., "Recurrent Mutations in a Single Exon Encoding the Evolutionarily Conserved Olfactomedin-Homology Domain of TIGR in Familial Open-Angle Glaucoma," *Human Molecular Genetics*, 6(12):2091–2097 (1997)). The 1q glaucoma gene (GLC1A, TIGR) is the subject of Nguyen, et al., U.S. Pat. No. 5,606,043, issued Feb. 25, 1997.

Glucocorticoids have been associated with the development of ocular hypertension and primary open angle glaucoma (Kass, et al., "Corticosteroid-Induced Glaucoma, In Ritch, R., Shields, M. B., Krupin, T. (eds.)," *The Glaucomas*, The C. V. Mosby Company, St. Louis, Mo., pp. 1161–1168 (1989); DeSantis, et al., Dexamethasone-Induction of Ocular Hypertension in the Primate, *ARVO Abstracts. Invest. Ophthalmol Vis. Sci.*, 31(Suppl.):99 (1990); Knepper, et al., "Intraocular Pressure and Glycosaminoglycan Distribution in the Rabbit Eye: Effect of Age and Dexamethasone," *Exp. Eye Res.*, 27:567–575 (1978); Francois, et al., Ultrastructural and Morphometric Study of Corticosteroid Glaucoma in Rabbits, *Ophthalmic Res.*, 16:168–178 (1984); Lorenzetti, O. J., "Effects of Corticosteroids on Ocular Dynamics in Rabbits," *J. Pharmacol Exp. Therap.*, 175:763–772 (1970); and Zhan, et al., "Steroid Glaucoma: Corticosteroid-Induced Ocular Hypertension in Cats," *Exp. Eye Res.*, 54:211–218 (1992)). Glaucoma patients have also been reported to have higher levels of the endogenous glucocorticoid, cortisol (Rozsival, et al., "Aqueous Humour and Plasma Cortisol Levels in Glaucoma and Cataract Patients," *Current Eye Research*, 1:391–396 (1981); Ray, et al., "Plasma Cortisol in Glaucoma," *Ann. Ophthalmol.*, 9:1151–1154 (1977); and Schwartz, et al., "Increased Plasma Free Cortisol in Ocular Hypertension and Open Angle Glaucoma," *Arch. Ophthalmol.*, 105:1060–1065 (1987)).

It is known that trabecular meshwork cells have glucocorticoid receptors and that glucocorticoid binding with these receptors causes a change in trabecular meshwork cell gene expression. Known manifestations of this change include a reorganization of the cytoskeleton (Wilson, et al., Dexamethasone Induced Ultrastructural Changes in Cultured Human Trabecular Meshwork Cells, *Cur. Eye Res.*, 12:783–793 (1993), and Clark, et al., "Glucocorticoid-Induced Formation of Cross-Linked Actin Networks in Cultured Human Trabecular Meshwork Cells," *Invest. Ophthalmol. Vis. Sci.*, 35:281–294 (1994)) and increased deposition of the extracellular matrix material in trabecular meshwork cells. As a result, the trabecular meshwork becomes "clogged" and unable to perform one of its most critical functions, that is, serving as a gateway for aqueous humor flow from the anterior chamber of the eye. When the aqueous humor flow out of the eye via the trabecular meshwork is diminished, the intraocular pressure of the eye rises. If this state of elevated intraocular pressure is maintained or frequently occurs, the optic nerve head can be damaged resulting in the loss of visual field. Loss of visual field is the hallmark symptom associated with glaucoma.

Endogenous glucocorticoids may be responsible for producing the changes in the trabecular meshwork that lead to ocular hypertension and glaucoma.

In summary, the GLC1A gene product can lead to the development of ocular hypertension and glaucoma in one of two ways: (1) mutations in GLC1A are responsible for most forms of juvenile glaucoma and a subset of adult onset POAG or (2) exposure of some individuals to glucocorticoids leads to increased GLC1A expression in the TM which causes increased aqueous humor outflow resistance and the development of ocular hypertension. The precise mechanism(s) responsible for GLC1A effects on IOP are currently unknown.

Steroids functioning to inhibit angiogenesis in the presence of heparin or specific heparin fragments are disclosed in Crum, et al., "A New Class of Steroids Inhibits Angiogenesis in the Presence of Heparin or a Heparin Fragment," *Science*, 230:1375–1378 (Dec. 20, 1985). The authors refer to such steroids as "angiostatic" steroids. Included within the new class of steroids found to be angiostatic are the dihydro and tetrahydro metabolites of cortisol and cortexolone. In a follow-up study directed to testing a hypothesis as to the mechanism by which the steroids inhibit angiogenesis, it was shown that heparin/angiostatic steroid compositions cause dissolution of the basement membrane scaffolding to which anchorage dependent endothelia are attached resulting in capillary involution; see, Ingber, et al., "A Possible Mechanism for Inhibition of Angiogenesis by Angiostatic Steroids: Induction of Capillary Basement Membrane Dissolution," *Endocrinology*, 119:1768–1775 (1986).

A group of tetrahydro steroids useful in inhibiting angiogenesis is disclosed in International Patent Application No. PCT/US86/02189, Aristoff, et al., (The Upjohn Company). The compounds are disclosed for use in treating head trauma, spinal trauma, septic or traumatic shock, stroke and hemorrhage shock. In addition, the patent application discusses the utility of these compounds in embryo implantation and in the treatment of cancer, arthritis and arteriosclerosis. The compounds are not disclosed for ophthalmic use.

Tetrahydrocortisol (THF) has been disclosed for its use in lowering the intraocular pressure (IOP) of rabbits made hypertensive with dexamethasone alone, or with dexamethasone/5-beta-dihydrocortisol; see Southren, et al., "Intraocular Hypotensive Effect of a Topically Applied Cortisol Metabolite: 3-alpha, 5-beta-tetrahydrocortisol," *Investigative Ophthalmology and Visual Science*, 28 (May, 1987). The authors suggest THF may be useful as an antiglaucoma agent. In U.S. Pat. No. 4,863,912, issued to Southren et al. on Sep. 5, 1989, pharmaceutical compositions containing THF and a method for using these compositions to control intraocular pressure are disclosed. THF has been disclosed as an angiostatic steroid in Folkman, et al., "Angiostatic Steroids," *Ann. Surg.*, 206(3) (1987) wherein it is suggested angiostatic steroids may have potential use for diseases dominated by abnormal neovascularization, including diabetic retinopathy, neovascular glaucoma and retrolental fibroplasia.

SUMMARY OF THE INVENTION

Angiostatic steroids and their pharmaceutical formulations are useful for treating GLC1A glaucoma. The invention is also directed to methods for controlling GLC1A glaucoma using angiostatic steroids.

DETAILED DESCRIPTION OF PREFERRED EMBODIMENTS

Agents which alter the expression of GLC1A in the glaucomatous eye are expected to lower IOP and thereby prevent or inhibit the glaucomatous optic neuropathy which is being driven by elevated IOP. Glucocorticoids upregulte GLC1A expression in the TM of certain individuals. There have been several reports of elevated levels of the natural glucocorticid cortisol in the aqueous humor and plasma of glaucoma patients (Schwartz, et al., supra, Rozsival, et al., supra). In addition, certain mutations in GLC1A may alter the expression of GLC1A in the TM tissue of 1q glaucoma patients. Unexpectedly, it has been discovered that angiostatic agents inhibit the expression of GLC1A in cultured human TM cells and lower elevated IOP in certain animal models of ocular hypertension. The compounds thereby prevent the expression of GLC1A and the subsequent development of ocular hypertension.

The development of blood vessels for the purpose of sustaining viable tissue is known as angiogenesis. Agents which inhibit angiogenesis are known by a variety of terms such as angiostatic, angiolytic or angiotropic agents. For purposes of this specification, the term "angiostatic agent" means compounds which can be used to inhibit angiogenesis.

The specific angiostatic agents of the present invention are steroids or steroid metabolites. For purposes herein, the term "angiostatic steroids" means steroids and steroid metabolites which inhibit angiogenesis. The present invention is based on the finding that angiostatic steroids can be used for the control of ocular hypertension. In particular, the agents can be used for the treatment of GLC1A glaucoma.

Preferred angiostatic steroids of the present invention have the following formula:

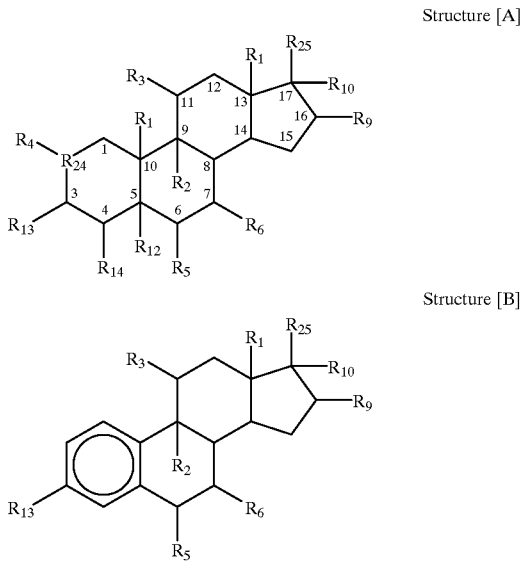

Structure [A]

Structure [B]

wherein $R_1$ is H, $\beta$-$CH_3$ or $\beta$-$C_2H_5$;

$R_2$ is F, $C_9$–$C_{11}$ double bond, $C_9$–$C_{11}$ epoxy, H or Cl;

$R_3$ is H, $OR_{26}$, $OC(=O)R_{27}$, halogen, $C_9$–$C_{11}$ double bond, $C_9$–$C_{11}$ epoxy, =O, —OH, —O-alkyl($C_1$–$C_{12}$), —OC(=O)alkyl($C_1$–$C_{12}$), —OC(=O)ARYL, —OC(=O)N(R)$_2$ or —OC(=O)OR$_7$, wherein ARYL is furyl, thienyl, pyrrolyl, or pyridyl and each of said moieties is optionally substituted with one or two ($C_1$–$C_4$)alkyl groups, or ARYL is —(CH$_2$)$_f$-phenyl wherein f is 0 to 2 and the phenyl ring is optionally substituted with 1 to 3 groups selected from chlorine, fluorine, bromine, alkyl($C_1$–$C_3$), alkoxy($C_1$–$C_3$), thioalkoxy-($C_1$–$C_3$), Cl$_3$C—, F$_3$C—, —NH$_2$ and —NHCOCH$_3$ and R is hydrogen, alkyl($C_1$–$C_4$), or phenyl and each R can be the same or different, and $R_7$ is ARYL as herein defined, or alkyl($C_1$–$C_{12}$);

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is $CH_2CH_2OR_{26}$, $CH_2CH_2OC(=O)R_{27}$, H, OH, $CH_3$, F, =$CH_2$, $CH_2C(=O)OR_{28}$, $OR_{26}$, $O(C=O)R_{27}$ or $O(C=O)CH_2C(=O)OR_{26}$ $R_{10}$ is —C≡CH, —CH=CH$_2$, halogen, CN, N$_3$, $OR_{26}$, $OC(=O)R_{27}$, H, OH, $CH_3$ or $R_{10}$ forms a second bond between positions C-16 and C-17;

$R_{12}$ is H or forms a double bond with $R_1$ or $R_{14}$;

$R_{13}$ is halogen, $OR_{26}$, $OC(=O)R_{27}$, $NH_2$, $NHR_{26}$, NHC(=O)R$_{27}$, N(R$_{26}$)$_2$, NC(=O)R$_{27}$, N$_3$, H, —OH, =O, —O—P(=O)(OH)$_2$, or —O—C(=O)—(CH$_2$)$_t$COOH where t is an integer from 2 to 6;

$R_{14}$ is H or forms a double bond with $R_{12}$;

$R_{15}$ is H, =O or —OH;

and $R_{23}$ with $R_{10}$ forms a cyclic phosphate;

wherein $R_9$ and $R_{15}$ have the meaning defined above;

or wherein $R_{23}$ is —OH, O—C(=O)—$R_{11}$, —OP(O)—(OH)$_2$, or —O—C(=O)—(CH$_2$)$_t$COOH wherein t is an integer from 2 to 6; and $R_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond, —CON(R$_{18}$)—, —N(R$_{18}$)CO—, —O—, —S—, —S(O)—, or —S(O$_2$)—; $R_{18}$ is hydrogen or alkyl ($C_1$–$C_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocyclic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —R$_{19}$—CH$_2$COOH wherein $R_{19}$ is —S—, —S(O)—, —S(O)$_2$—, —SO$_2$N(R$_{20}$)—, or N(R$_{20}$)SO$_2$—; and $R_{20}$ is hydrogen or lower alkyl-($C_1$–$C_4$); with the proviso that the total number of carbon atoms in $R_{20}$ and (CH$_2$)$_r$ is not greater than 10; or (2) —CO—COOH; or (3) CON(R$_{21}$)CH(R$_{22}$)COOH wherein $R_{21}$ is H and $R_{22}$ is H, $CH_3$, —CH$_2$COOH, —CH$_2$CH$_2$COOH, —CH$_2$OH, —CH$_2$SH, —CH$_2$CH$_2$SCH$_3$, or —CH$_2$Ph-OH wherein Ph-OH is p-hydroxyphenyl;

or $R_{21}$ is $CH_3$ and $R_{22}$ is H;

or $R_{21}$ and $R_{22}$ taken together are —CH$_2$CH$_2$CH$_2$—;

or —N(R$_{21}$)CH(R$_{22}$)COOH taken together is —NHCH$_2$CONHCH$_2$COOH; and pharmaceutically acceptable salts thereof;

with the proviso that if $R_{23}$ is a phosphate, it must form a cyclic phosphate, with $R_{10}$ when $R_{13}$ is =O, except for the compound wherein $R_1$ is $\beta$-$CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is —F, $R_9$ is $\beta$-$CH_3$, $R_{10}$ is -OH, $R_{13}$ and $R_{15}$ are =O and $R_{23}$ is —OP(O)—(OH)$_2$.

$R_{24}$=C, $C_1$–$C_2$ double bond, O;

$R_{25}$=C(R$_{15}$)CH$_2$—R$_{23}$, OH, OR$_{26}$, OC(=O)R$_{27}$, R$_{26}$, COOH, C(=O)OR$_{26}$, CHOHCH$_2$OH, CHOHCH$_2$OR$_{26}$, CHOHCH$_2$OC(=O)R$_{27}$, CH$_2$CH$_2$OH, CH$_2$CH$_2$OR$_{26}$, CH$_2$CH$_2$OC(=O)R$_{27}$, CH$_2$CN, CH$_2$N$_3$, CH$_2$NH$_2$, CH$_2$NHR$_{26}$, CH$_2$N(R$_{26}$)$_2$, CH$_2$OH, CH$_2$OR$_{26}$, CH$_2$O(C=O)R$_{27}$, CH$_2$O(P=O)(OH)$_2$, CH$_2$O(P=O)(OR$_{26}$)$_2$, CH$_2$SH, CH$_2$S—R$_{26}$, CH$_2$SC(=O)R$_{27}$, CH$_2$NC(=O)R$_{27}$, C(=O)CHR$_{28}$OH, C(=O)CHR$_{28}$OR$_{26}$, C(=O)CHR$_{28}$OC(=O)R$_{27}$ or $R_{10}$ and $R_{25}$ taken together may be =C(R$_{28}$)$_2$, that is, an optionally alkyl substituted methylene group;

wherein $R_{26}$=$C_1$–$C_6$ (alkyl, branched alkyl, cycloalkyl, haloalkyl, aralkyl, aryl); $R_{27}$=$R_{26}$+$OR_{26}$; $R_{28}$=H, $C_1$–$C_6$ (alkyl, branched alkyl, cycloalkyl).

Unless specified otherwise, all substituent groups attached to the cyclopentanophenanthrene moiety of Structures [A] and [B] may be in either the alpha or beta position. Additionally, the above structures include all pharmaceutically acceptable salts of the angiostatic steroids.

Preferred angiostatic steroids are:

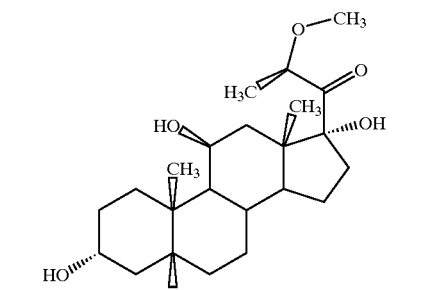

21-METHYL-5β-PREGNAN-3α,11β,17α,
21-TETROL-20-ONE 21-METHYL ETHER

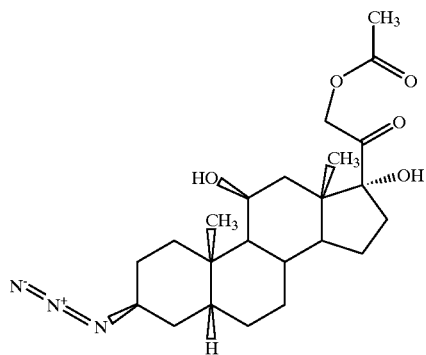

3β-AZIDO-5β-PREGNAN-11β,
17α,21-TRIOL-20-ONE-21-ACETATE

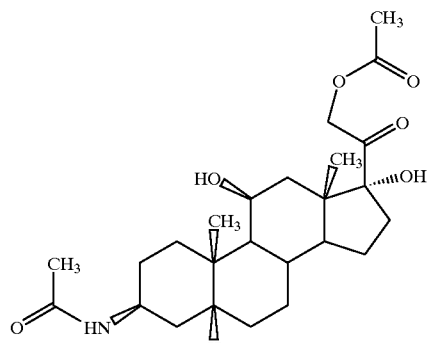

3β-ACETAMIDO-5β-PREGNAN-
11β,17α,21-TRIOL-20-ONE
21-ACETATE

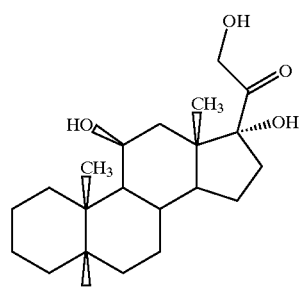

5β-PREGNAN-11β,17α,21-TRIOL-20-ONE

-continued

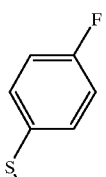

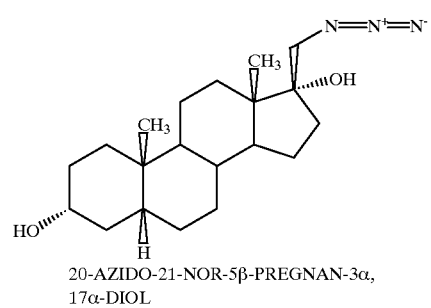

17-((4-FLUORO)THIOPHENOXY)METHYL-
1,3,5-ESTRATRIEN-3,17-DIOL

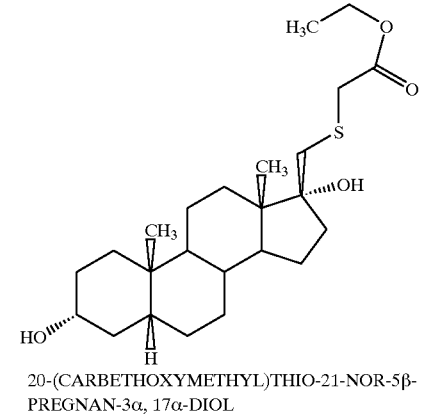

20-AZIDO-21-NOR-5β-PREGNAN-3α,
17α-DIOL

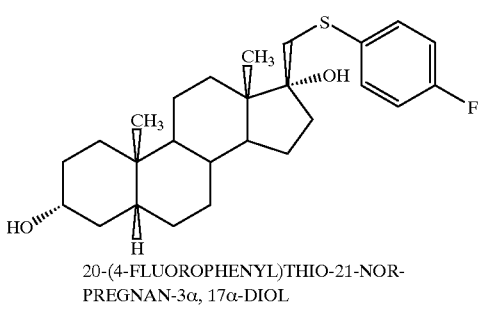

20-(CARBETHOXYMETHYL)THIO-21-NOR-5β-
PREGNAN-3α, 17α-DIOL 20-(4-FLUOROPHENYL)THIO-21-NOR-
PREGNAN-3α, 17α-DIOL

-continued
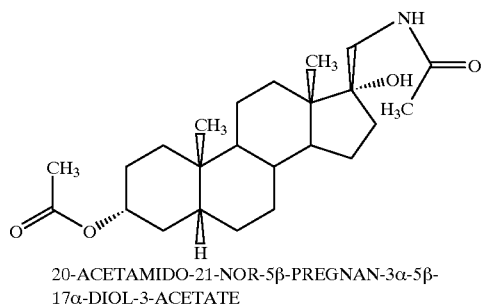
20-ACETAMIDO-21-NOR-5β-PREGNAN-3α-5β-17α-DIOL-3-ACETATE
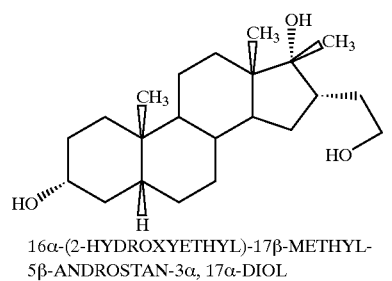
16α-(2-HYDROXYETHYL)-17β-METHYL-5β-ANDROSTAN-3α, 17α-DIOL
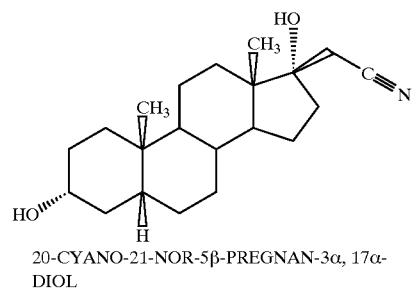
20-CYANO-21-NOR-5β-PREGNAN-3α, 17α-DIOL
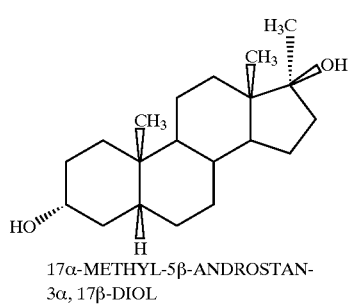
17α-METHYL-5β-ANDROSTAN-3α, 17β-DIOL
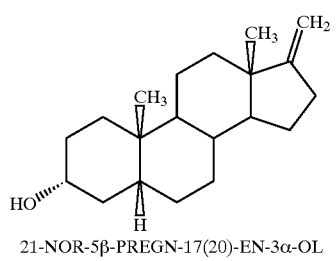
21-NOR-5β-PREGN-17(20)-EN-3α-OL
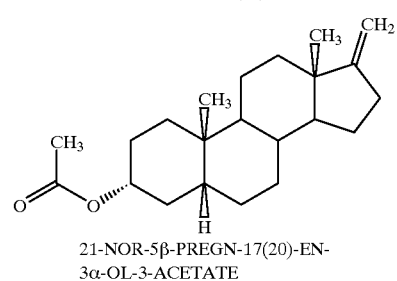
21-NOR-5β-PREGN-17(20)-EN-3α-OL-3-ACETATE
-continued
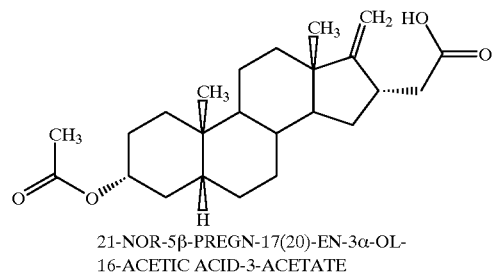
21-NOR-5β-PREGN-17(20)-EN-3α-OL-16-ACETIC ACID-3-ACETATE
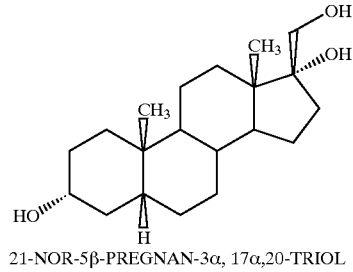
21-NOR-5β-PREGNAN-3α, 17α,20-TRIOL
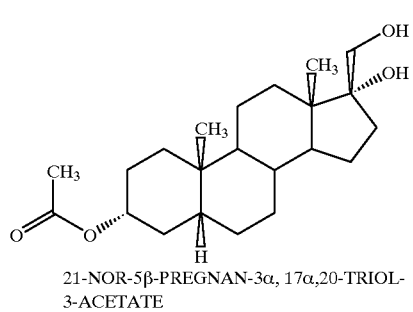
21-NOR-5β-PREGNAN-3α, 17α,20-TRIOL-3-ACETATE
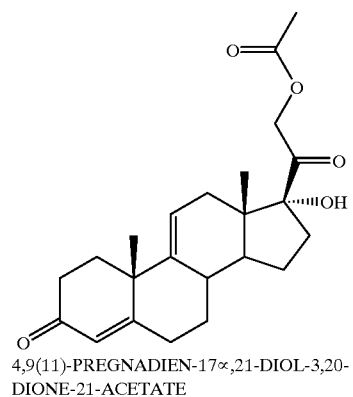
4,9(11)-PREGNADIEN-17α,21-DIOL-3,20-DIONE-21-ACETATE
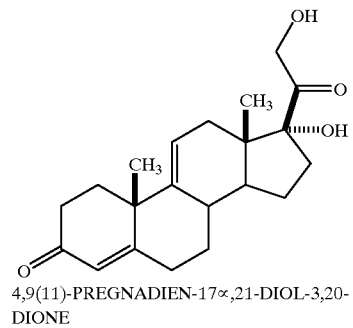
4,9(11)-PREGNADIEN-17α,21-DIOL-3,20-DIONE The more preferred compounds are 21-methyl-5β-pregnan-3,11β,17,21-tetrol 20-one-21-methyl ether; 3β-azido-21-acetoxy-5β-pregnan-11β,17-diol-20-one; 3β-acetamido-21-acetoxy-5β-pregnan-11β,17-diol-20-one; and 5β-pregnan-11β,17,21-triol-20-one. The most preferred compounds are 4,9(11)-pregnadien-17β,21-diol-3,20-dione-21-acetate and 4,9(11)-pregnadien-17,21-diol-3,20-dione.

The angiostatic steroids of the present invention may be incorporated in various formulations for delivery to the eye. For example, topical formulations can be used and can include ophthalmologically acceptable preservatives, surfactants, viscosity enhancers, buffers, sodium chloride and water to form aqueous sterile ophthalmic solutions and suspensions. In order to prepare sterile ophthalmic ointment formulations, an angiostatic steroid is combined with a preservative in an appropriate vehicle, such as mineral oil, liquid lanolin or white petrolatum. Sterile ophthalmic gel formulations comprising the angiostatic steroids of the present invention can be prepared by suspending an angiostatic steroid in a hydrophilic base prepared from a combination of, for example, Carbopol-940 (a carboxyvinyl polymer available from the B. F. Goodrich Company) according to published formulations for analogous ophthalmic preparations. Preservatives and tonicity agents may also be incorporated in such gel formulations.

The specific type of formulations selected will depend on various factors, such as the angiostatic steroid or its salt being used, and the dosage frequency. Topical ophthalmic aqueous solutions, suspensions, ointments and gels are the preferred dosage forms. The angiostatic steroid will normally be contained in these formulations in an amount of from about 0.005 to about 5.0 weight percent (wt. %). Preferable concentrations range from about 0.05 to about 2.0 wt. %. Thus, for topical administration, these formulations are delivered to the surface of the eye one to four times per day, depending upon the routine discretion of the skilled clinician.

The following examples illustrate formulations and synthesis of compounds of the present invention, but are in no way limiting.

| Component | wt. % |
| --- | --- |
| Angiostatic Steroid | 0.005–5.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 2

| Component | wt. % |
| --- | --- |
| 4,9(11)-pregnadien-17,21-diol-3,20-dione-21-acetate | 1.0 |
| Mannitol | 2.40 |
| Carbopol 974P | 0.50 |
| Polysorbate 80 | 0.05 |
| Benzalkonium Chloride | 0.01 |
| Sodium Chloride | 0.4 |
| Edetate Disodium | 0.01 |
| NaOH/HCl | q.s. pH 7.4 |
| Purified Water | q.s. 100 mL |

EXAMPLE 3

Preparation of 5β-Pregnan-11β,17,21-triol-20-one Tetrahydrocortisol-F-21-t-butyldiphenylsilyl ether (PS03842)

A solution of 4.75 g (17.3 mmol) of t-butyldiphenylchlorosilane in 5 mL of dry DMF was added dropwise to a stirred solution of 5.7 g (15.6 mmol) of tetrahydrocortisol-F (Steraloids No. P9050) and 2.3 g (19 mmol) of 4-dimethylaminopyridine (DMAP) in 30 mL of dry DMF, under $N_2$, at −25 to −30° C. (maintained with $CO_2$—MeCN). After a further 20 min at −30° C., the mixture was allowed to warm to 23° C. overnight.

The mixture was partitioned between ether and water, and the organic solution was washed with brine, dried ($MgSO_4$), filtered and concentrated to give 10.7 g of a white foam.

This material was purified by flash column chromatography (400 g silica; 62.5 to 70% ether/hexane). The 3-siloxy isomer eluted first, followed by mixed fractions, followed by the title compound. The concentrated mixed fractions (4.0 g) were chromatographed on the same column with 35% ethyl acetate/hexane. The total yield of the 3-siloxy isomer was 0.42 g (5%), and of the title compound, 5.05 g (53.5%). Continued elution with 25% MeOH/EtOAc allowed recovery of unreacted tetrahydrocortisol-F.
PS03842

NMR (200 MHz $^1$H) (CDCl$_3$): δ0.63 (s, 3H, Me-18); 1.11 (s, 9H, t-Bu); 1.12 (s, 3H, Me-19); 2.57 (t, J=13, 1H, H-8); 2.6 (s, 1H, OH-17); 3.63 (sept, J=2.5, 1H, H-3); 4.15 (br s, 1H, H-11); 4.37 and 4.75 (AB, J=20, 2H, H-21); 7.4 (m, 6H) and 7.7 (m, 4H) (Ph$_2$).

NMR (200 MHz $^1$H) (DMSO-d$_6$): δ0.64 (s, 3H, Me-18); 1.02 (s, 9H, t-Bu); 1.07 (s, 3H, Me-19); 2.50 (t, J=13, 1H, H-8); 3.37 (m, 1H, H-3); 3.94 (d, J=2, 1H, OH-11); 4.00 (br s, 1H, H-11); 4.42 (d, J=5, 1H, OH-3); 4.38 and 4.83 (AB, J=20, 2H, H-21); 5.11 (s, 1H, OH-17); 7.45 (m, 6H) and 7.6 (m, 4H) (Ph$_2$).

NMR (50.3-MHz $^{13}$C) (CDCl$_3$): 17.4 (C-18); 19.3 (C-16); 23.7 (C-15); 26.3 (C-7); 26.6 (C-19); 26.8 (Me$_3$C); 27.2 (C-6); 30.9 (C-2); 31.5 (C-8); 34.1 (Me$_3$C); 34.8 (C-10); 35.2 (C-1); 36.2 (C-4); 39.7 (C-13); 43.5 (C-5); 44.3 (C-9); 47.4 (C-12); 52.1 (C-14); 67.8 (C-11); 68.9 (C-21); 71.7 (C-3); 89.8 (C-14); 127.8, 129.8, 132.8, 132.9, 135.7, 135.8 (diastereotopic Ph$_2$); 208.8 (C-20). Underlined resonances showed inversion in the APT experiment. Assignments: E. Breitmaier, W. Voelter "Carbon-13 NMR Spectroscopy," 3d ed., VCH, 1987; pp. 345–348.

IR (KBr) 3460, 2930, 2860, 1720, 1428, 1136, 1113, 1070, 1039, 703 cm$^{-1}$.

This compound did not show a sharp melting point but turned to a foam at 80–100° C. Numerous attempts at recrystallization failed.

5β-Pregnan-11β,17,21-triol-20-one

A solution of PS03842 (0.91 g, 1.50 mmol) and thiocarbonyl diimidazole (1.05 g, 5.9 mmol) in 8 mL of anhydrous dioxane was refluxed under $N_2$ for 3.5 h. The cooled solution was partitioned between ether and water and the organic solution was washed with brine, dried (MgSO$_4$), filtered and concentrated. The residue was chromatographed (120 g SiO$_2$, 35% EtOAc/hexane) giving 0.86 g (80%) of the imidazolyl thioester.

A solution of 0.75 g (1.05 mmol) of this compound in 100 mL of anhydrous dioxane was added dropwise over 2.2 h to a rapidly stirred, refluxing solution of 1.6 mL (5.9 mmol) of Bu$_3$SnH in 100 mL of anhydrous dioxane under $N_2$. After a further 1 h at reflux, the solution was cooled, concentrated and the residue chromatographed (200 g SiO$_2$, 9% EtOAc/hexane) giving 0.43 g (70%) of the 3-deoxy-21-silyl ether.

This material was dissolved in 20 mL of methanol; Bu$_4$NF·3H$_2$O (0.50 g, 1.6 mmol) was added, and the mixture was heated to reflux under N$_2$ for 4 h. The cooled solution was diluted with 2 volumes of EtOAc, concentrated to ¼ volume, partitioned (EtOAc/H$_2$O), and the organic solution was washed with brine, dried (MgSO$_4$), filtered and concentrated. The residue (0.40 g) was chromatographed (30 g SiO$_2$, 40% EtOAc/hexane) to give 0.25 g (98%) of an oil.

This oil was crystallized (n-BuCl) to afford 0.14 g of the title compound as a white solid, m.p. 167–170° C.

IR (KBr): 3413 (br), 2934, 1714, 1455, 1389, 1095, 1035 cm$^-$.

MS (Cl): 351 (M+1).

NMR (200 MHz $^1$H, DMSO-d$_6$): δ0.69 (s, 3H, Me-18); 1.14 (s, 3H, Me-19); 0.8–2.0 (m); 2.5 (t, J=13, 1H, H-8); 3.96 (d, J=2, 1H, OH-11); 4.1 (br s, 1H, H-11); 4.1 and 4.5 (AB, further split by 5 Hz, 2H, H-21); 4.6 (t, J=5, 1H, OH-21); 5.14 (s, 1H, OH-17).

Anal. Calc'd for C$_{21}$H$_{34}$O$_4$: C, 71.96; H, 9.78. Found: C, 71.69; H, 9.66.

EXAMPLE 4

Preparation of 21-Methyl-5β-pregnan-3,11β,17, 21-tetrol-20-one 21-methyl ether

Sodium hydride (60% oil dispersion, 0.10 g, 2.5 mmol) was added to a stirred solution of tetrahydrocortisol-F (0.73 g, 2.0 mmol) and CH$_3$I (0.60 mL, 9.6 mmol) in 8 mL of anhydrous DMF under N$_2$. Hydrogen was evolved, and the temperature rose to 35° C. After 1 h, the mixture was diluted with EtOAc, extracted with water (until neutral) and brine, dried (MgSO$_4$), filtered and concentrated. The residue was chromatographed (70 g SiO$_2$, 80% EtOAc/hexane) to give 0.17 g of a white solid, MS (Cl)=395 (M+1). This material was recrystallized (EtOAc-n-BuCl) to afford 0.12 g (16%) of the title compound as a feathery white solid, m.p. 208–213° C.

IR (KBr): 3530, 3452, 2939, 2868, 1696 (s, CO), 1456, 1366, 1049 cm$^{-1}$.

NMR (200 MHz $^1$H, DMSO-d$_6$): δ0.74 (s, 3H, Me-18); 1.09 (s, 3H, Me-19); 1.14 (d, J=6.6, 3H, C-21 Me); 0.8–2.0 (m); 2.47 (t, J=13, 1H, H-8); 3.18 (s, 3H, OMe); 3.35 (m, 1H, H-3); 4.00 (d, J=2, 1H, OH-11); 4.07 (brs, 1H, H-11); 4.37 (q, J=6.6, 1H, H-21); 4.43 (d, J=5, 1H, OH-3); 5.16 (s, 1H, OH-17).

Anal. Calc'd for C$_{23}$H$_{38}$O$_5$: C, 70.01; H, 9.71. Found: C, 70.06; H, 9.76.

EXAMPLE 5

Preparation of 3β-Azido-21-acetoxy-5β-pregnan-11β,17-diol-20-one

A solution of triphenylphosphine (2.6 g, 10 mmol) in 10 mL of toluene was carefully added to a stirred solution of PSO3842 (see Example 4) (1.75 g, 2.90 mmol), diphenylphosphoryl azide (2.2 mL, 10.2 mmol) and diethyl azodicarboxylate (1.55 mL, 10 mmol) under N$_2$, keeping the internal temperature below 35° C. (exothermic). The solution was stirred for 1.2 h, then diluted with ether, washed with water and brine, dried (MgSO$_4$), filtered and concentrated and the residue (9.5 g, oil) chromatographed 175 g SiO$_2$, 15% EtOAc/hexane) giving 1.83 g of a viscous oil.

A solution of 1.73 g of this material and 1.75 g (5.5 mmol) of Bu$_4$NF·3H$_2$O in 20 mL of methanol was refluxed under N$_2$ for 2.5 h. The crude product (1.94 g) was isolated with ethyl acetate and chromatographed (100 g SiO$_2$, 50% EtOAc/hexane) giving 0.60 g (56%) of a white semisolid. Trituration (4:1 hexane-ether) gave 0.57 g (53%) of a solid.

A stirred solution of 0.40 g of this material in 3 mL of dry pyridine was treated with 0.3 mL of acetic anhydride and stirred overnight at 23° C. under N$_2$. The mixture was quenched with 1 mL of methanol, stirred for 15 min, diluted with ether, washed with 1 M aqueous HCl, water (until neutral), brine, dried (MgSO4), filtered and concentrated. The residue (0.41 g, oil) was chromatographed (35 g SiO$_2$, 33% EtOAc/hexane) to afford 0.33 g (76%) of the title compound as a white foam, m.p. 80–90° C. (dec).

IR (KBr): 3505, 2927, 2866, 2103 (vs), 1721 (sh 1730), 1268, 1235 cm$^{-1}$.

NMR (200 MHz $^1$H, CDCl$_3$): δ0.92 (s, 3H, Me-18); 1.21 (s, 3H, Me-19); 1.0–2.1 (m); 2.17 (s, 3H, Ac); 2.25 (s 1H, OH-17); 2.74 (m, 1H, H-8); 3.97 (br s, 1H, H-3); 4.31 (br s, 1H, H-11); 4.94 (AB, J=17, Δv=60, 2H, H-21).

Anal. Calc'd for C$_{23}$H$_{35}$N$_3$O$_5$: C, 63.72; H, 8.14; N, 9.69. Found: C, 63.39; H, 8.18; N, 9.45.

EXAMPLE 6

Preparation of 3β-Acetamido-21-acetoxy-5β-pregnan-11β,17-diol-20-one

A solution of 3β-azido-21-acetoxy-5β-pregnan-11β,17-diol-20-one (0.15 g, 0.35 mmol) in 8 mL of absolute ethanol containing 0.03 g of 10% Pd on C was stirred under H$_2$ (1 atm) at 23° C. for 2 h. The mixture was filtered and concentrated, the residue dissolved in EtOAc, the basic material extracted into 1 M aqueous HCl, liberated (Na$_2$CO$_3$), extracted (EtOAc) and the organic extract washed with water (until neutral) and brine, dried (MgSO$_4$), filtered and concentrated to provide 58 mg of a solid.

This material was acetylated (1.0 mL of dry pyridine, 0.20 mL of Ac$_2$O, 23° C., N$_2$, overnight), followed by workup (as described for the steroid of Example 6 [last step]) affording a crude product that was chromatographed (25 g SiO$_2$, EtOAc). This product was triturated with ether to afford 51 mg (33%) of product as a white solid, m.p. 179–181° C.

Ms (Cl, isobutane): (M+1)=450 (M$^+$), 432, 391, 371, 348.

IR (KBr): 3398 (br), 2932, 2865, 1720 (sh. 1740), 1652, 1538, 1375, 1265, 1236 cm$^{-1}$.

NMR (200 MHz $^1$H, CDCl$_3$): δ0.89, 1.22, 1.99, 2.17 (all s, 3H); 1.0–2.2 (m); 2.7 (t, J=13, 1H, H-8); 3.03 (s, 1H, OH-17); 4.2 (br s, 1H, H-11); 4.3 (br s, 1H, H-3); 4.96 (AB, J=17.5, Δv=42, 2H, H-21); 5.8 (d, J=10, 1H, NH).

We claim:

1. A method for treating GLC1A glaucoma which comprises administering to a person in need thereof a pharmaceutically effective amount of angiostatic agent that has the following structure:

Structure [A]

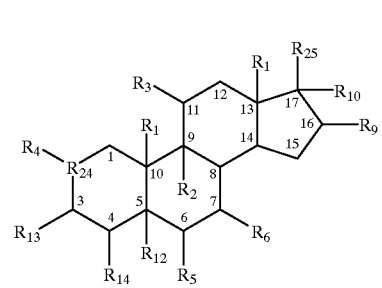

-continued

Structure [B]

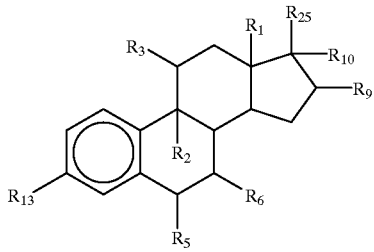

wherein $R_1$ is H, $\beta$-$CH_3$ or $\beta$-$C_2H_5$;

$R_2$ is F, $C_9$–$C_{11}$ double bond, $C_9$–$C_{11}$ epoxy, H or Cl;

$R_3$ is H, $OR_{26}$, $OC(=O)R_{27}$, halogen, $C_9$–$C_{11}$ double bond, $C_9$–$C_{11}$ epoxy, =O, —OH, —O-alkyl($C_1$–$C_{12}$), —OC(=O)alkyl($C_1$–$C_{12}$), —OC(=O)ARYL, —OC(=O)N(R)$_2$ or —OC(=O)OR$_7$, wherein ARYL is furyl, thienyl, pyrrolyl, or pyridyl and each of said moieties is optionally substituted with one or two ($C_1$–$C_4$)alkyl groups, or ARYL is —(CH$_2$)$_f$-phenyl wherein f is 0 to 2 and the phenyl ring is optionally substituted with 1 to 3 groups selected from chlorine, fluorine, bromine, alkyl($C_1$–$C_3$), alkoxy($C_1$–$C_3$), thioalkoxy-($C_1$–$C_3$), $Cl_3C$—, $F_3C$—, —$NH_2$ and —$NHCOCH_3$ and R is hydrogen, alkyl ($C_1$–$C_4$), or phenyl and each R can be the same or different, and $R_7$ is ARYL as herein defined, or alkyl($C_1$–$C_{12}$);

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is $CH_2CH_2OR_{26}$, $CH_2CH_2OC(=O)R_{27}$, H, OH, $CH_3$, F, =$CH_2$, $CH_2C(=O)OR_{28}$, $OR_{26}$, $O(C=O)R_{27}$ or $O(C=O)CH_2C(=O)OR_{26}$ $R_{10}$ is —C≡CH, —CH=$CH_2$, halogen, CN, $N_3$, $OR_{26}$, $OC(=O)R_{27}$, H, OH, $CH_3$ or $R_{10}$ forms a second bond between positions C-16 and C-17;

$R_{12}$ is H or forms a double bond with $R_1$ or $R_{14}$;

$R_{13}$ is halogen, $OR_{26}$, $OC(=O)R_{27}$, $NH_2$, $NHR_{26}$, NHC(=O)$R_{27}$, N($R_{26}$)$_2$, NC(=O)$R_{27}$, $N_3$, H, —OH, =O, —O—P(=O)(OH)$_2$, or —O—C(=O)—(CH$_2$)$_t$COOH where t is an integer from 2 to 6;

$R_{14}$ is H or forms a double bond with $R_{12}$;

$R_{15}$ is H, =O or —OH;

and $R_{23}$ with $R_{10}$ forms a cyclic phosphate;

wherein $R_9$ and $R_{15}$ have the meaning defined above;

or wherein $R_{23}$ is —OH, O—C(=O)—$R_{11}$, —OP(O)—(OH)$_2$, or —O—C(=O)—(CH$_2$)$_t$COOH wherein t is an integer from 2 to 6; and $R_{11}$ is —Y—(CH$_2$)$_n$—X—(CH$_2$)$_m$—$SO_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond, —CON($R_{18}$)—, —N($R_{18}$)CO—, —O—, —S—, —S(O)—, or —S(O$_2$)—; $R_{18}$ is hydrogen or alkyl ($C_1$–$C_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocyclic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —$R_{19}$—$CH_2$COOH wherein $R_{19}$ is —S—, —S(O)—, —S(O)$_2$—, —$SO_2$N($R_{20}$)—, or N($R_{20}$)$SO_2$—; and $R_{20}$ is hydrogen or lower alkyl-($C_1$–$C_4$); with the proviso that the total number of carbon atoms in $R_{20}$ and (CH$_2$)$_r$ is not greater than 10; or (2) —CO—COOH; or (3) CON($R_{21}$)CH($R_{22}$)COOH wherein $R_{21}$ is H and $R_{22}$ is H, $CH_3$, —$CH_2$COOH, —$CH_2CH_2$COOH, —$CH_2$OH, —$CH_2$SH, —$CH_2CH_2SCH_3$, or —$CH_2$Ph-OH wherein Ph-OH is p-hydroxyphenyl;

or $R_{21}$ is $CH_3$ and $R_{22}$ is H;

or $R_{21}$ and $R_{22}$ taken together are —$CH_2CH_2CH_2$—;

or —N($R_{21}$)CH($R_{22}$)COOH taken together is —$NHCH_2CONHCH_2$COOH; and pharmaceutically acceptable salts thereof;

with the proviso that if $R_{23}$ is a phosphate, it must form a cyclic phosphate, with $R_{10}$ when $R_{13}$ is =O, except for the compound wherein $R_1$ is $\beta$-$CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is —F, $R_9$ is $\beta$-$CH_3$, $R_{10}$ is -OH, $R_{13}$ and $R_{15}$ are =O and $R_{23}$ is —OP(O)—(OH)$_2$, $R_{24}$=C, $C_1$–$C_2$ double bond, O;

$R_{25}$=C($R_{15}$)$CH_2$—$R_{23}$, OH, $OR_{26}$, $OC(=O)R_{27}$, $R_{26}$, COOH, C(=O)OR$_{26}$, CHOHCH$_2$OH, CHOHCH$_2$OR$_{26}$, CHOHCH$_2$OC(=O)R$_{27}$, $CH_2CH_2$OH, $CH_2CH_2OR_{26}$, $CH_2CH_2OC(=O)R_{27}$, $CH_2$CN, $CH_2N_3$, $CH_2NH_2$, $CH_2NHR_{26}$, $CH_2$N($R_{26}$)$_2$, $CH_2$OH, $CH_2OR_{26}$, $CH_2O(C=O)R_{27}$, $CH_2$O(P=O)(OH)$_2$, $CH_2$O(P=O)(OR$_{26}$)$_2$, $CH_2$SH, $CH_2$S—$R_{26}$, $CH_2$SC(=O)R$_{27}$, $CH_2$NC(=O)R$_{27}$, C(=O)CHR$_{28}$OH, C(=O)CHR$_{28}$OR$_{26}$, C(=O)CHR$_{28}$OC(=O)R$_{27}$ or $R_{10}$ and $R_{25}$ taken together may be =C($R_{28}$)$_2$, that is, an optionally alkyl substituted methylene group;

wherein $R_{26}$=$C_1$–$C_6$ (alkyl, branched alkyl, cycloalkyl, haloalkyl, aralkyl, aryl);

$R_{27}$=$R_{26}$+$OR_{26}$; $R_{28}$=H, $C_1$–$C_6$ (alkyl, branched alkyl, cycloalkyl).

2. The method of claim 1 wherein the compound is selected from the group consisting of 21-methyl-5$\beta$-pregnan-3,11$\beta$,17,21-tetrol-20-one 21methyl ether; 3$\beta$-azido-21-acetoxy-5$\beta$-pregnan-11$\beta$,17-diol-20-one; 5$\beta$-pregnan-11$\beta$,∫,21-triol-20-one; 4,9(11)-pregnadien-17,21-diol-3,20-dione-21-acetate and 4,9(11)-pregnadien-17,21-diol-3,20-dione.

3. The method of claim 2 wherein the compound is selected from the group consisting of 4,9(11)-pregnadien-17,,21-diol-3,20-dione-21-acetate and 4,9(11)-pregnadien-17,21-diol-3,20-dione.

* * * * *